United States Patent [19]

Fujimoto et al.

[11] 4,219,477
[45] Aug. 26, 1980

[54] PENICILLIN DERIVATIVES

[75] Inventors: Yasuo Fujimoto, Tokyo; Yasuo Kishi, Misato, both of Japan

[73] Assignee: Nippon Chemiphar Company Limited, Tokyo, Japan

[21] Appl. No.: 966,628

[22] Filed: Dec. 5, 1978

[30] Foreign Application Priority Data

Dec. 6, 1977 [JP] Japan ........................ 52-145651
Dec. 22, 1977 [JP] Japan ........................ 52-153619
Aug. 21, 1978 [JP] Japan ........................ 52-100965

[51] Int. Cl.² ................ C07D 499/68; C07D 499/70
[52] U.S. Cl. ......................... 260/239.1; 424/246; 424/263; 424/271; 542/441; 542/443; 544/28; 544/30
[58] Field of Search ............... 260/239.1; 544/28, 30; 542/441, 443

[56] References Cited

U.S. PATENT DOCUMENTS

| | | | |
|---|---|---|---|
| 3,951,955 | 4/1976 | Tobiki et al. | 260/239.1 |
| 3,953,428 | 4/1976 | Murakami et al. | 260/239.1 |
| 4,112,090 | 9/1978 | Saikawa et al. | 260/239.1 |

*Primary Examiner*—Norman Morgenstern
*Assistant Examiner*—Vera C. Clarke
*Attorney, Agent, or Firm*—Oblon, Fisher, Spivak, McClelland & Maier

[57] ABSTRACT

Penicillin and cephalosporin derivatives and non-toxic salts thereof represented by the formula (1),

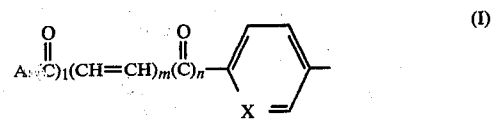

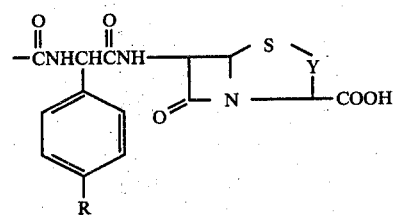

wherein Ar represents a phenyl or heterocyclic group which may be substituted by a halogen atom, or a hydroxy or lower alkoxy group, R represents a hydrogen atom or a hydroxy group, X represents CH or N,

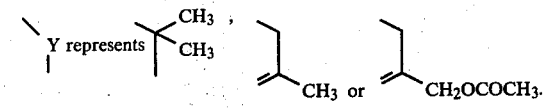

1 and n are integers of 0 or 1 wherein the sum equal to 1 and n is 0 or 1, and m is an integer equal to 1 or 2 are useful antibiotics.

16 Claims, No Drawings

PENICILLIN DERIVATIVES

BACKGROUND OF THE INVENTION

This invention relates to novel penicillin and cephlosporin derivatives and non-toxic salts thereof represented by the formula (I),

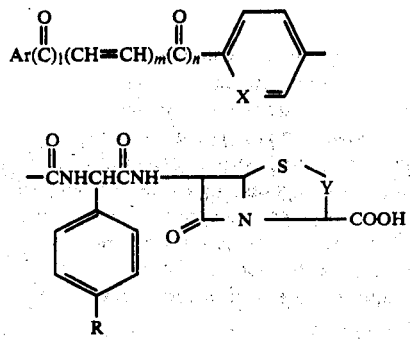

wherein Ar represents a phenyl or heterocyclic group which may be substituted by a halogen atom, or a hydroxy or lower alkoxy group, R represents a hydrogen atom or a hydroxy group, X represents CH or N,

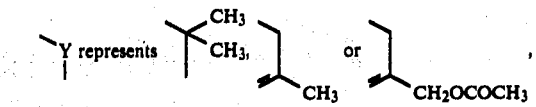

l and n are integers of 0 or 1 wherein the sum equal to 1 and n is 0 or 1, and m is an integer equal to 1 or 2.

SUMMARY OF THE INVENTION

It is an object of the invention to provide novel penicillin and cephalosporin derivatives and non-toxic salts thereof represented by the formula (I) which possess an excellent antibacterial effect and are useful for the treatment of bacterially caused diseases.

It is another object of the invention to provide a process for producing the above penicillin and cephalosporin derivatives and non-toxic salts thereof.

DETAILED DESCRIPTION OF THE PREFERRED EMBODIMENTS

Non-toxic salts of the compounds of the formula (I) include metallic salts such as sodium, potassium, magnesium, calcium and aluminum salts, and amine salts such as these with ammonia, a lower alkyl amine or a cyclic amine.

The compounds of the formula (I) involve optical isomers and among the D-, L- and DL-form, the D-form is particularly preferred.

The present compounds of the formula (I) are divided into the following groups according to the value of l, m and n:

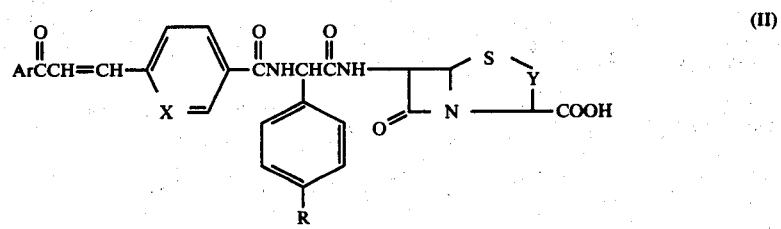

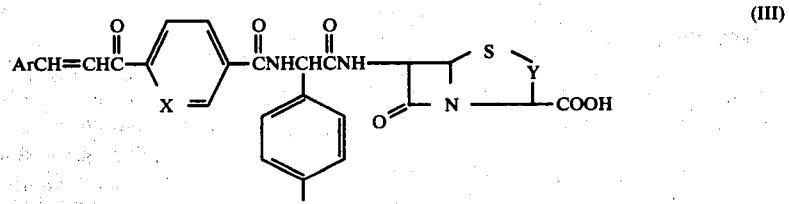

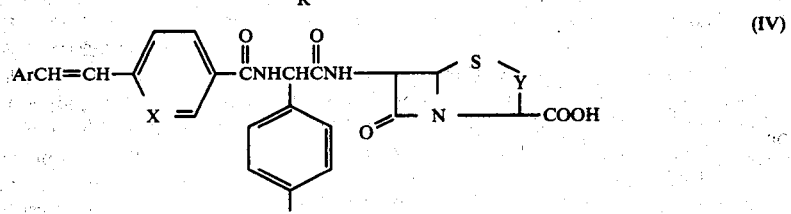

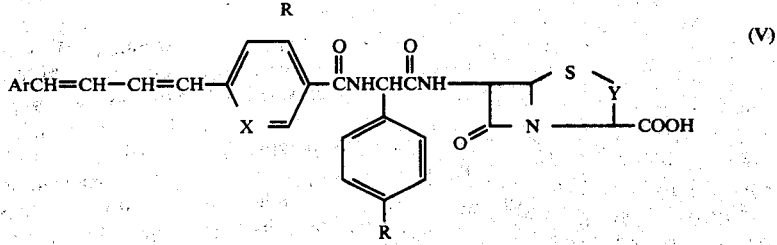

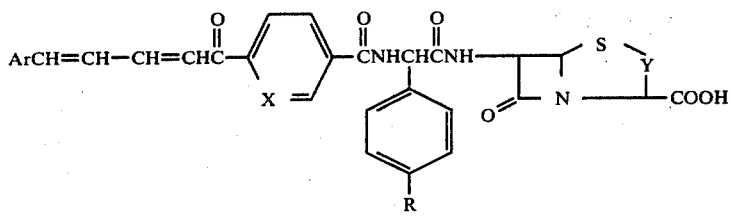

(VI)

wherein Ar, R, X and

are the same as defined above.

The compounds of the formula (I) and non-toxic salts thereof can be produced according to the following reaction scheme:

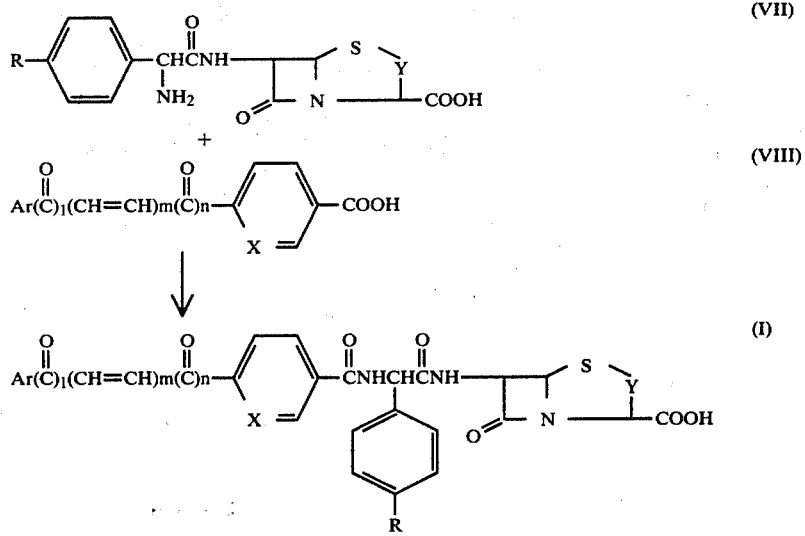

(VII)

(VIII)

(I)

wherein Ar, R, X,

l, m and n are the same as defined above.

That is, the compounds of the formula (I) are produced by reacting the compound of the formula (VII) or a salt thereof with the carboxylic acid of the formula (VIII) or a reactive derivative thereof. The compound of the formula (VII) may usually be used as a free acid or a water-soluble salt. However, the compound (VII) can also be advantageously used in which a protecting group is used at the 3- or 4-position which may be easily eliminated without the penicillin or cephalosporin structure being cleaved.

The protecting groups be used include those which are known to be useful for a carboxyl group, particularly for the production of penicillin-type and cephalosporin-type compounds, such as 2,2,2-trichloroethyl, p-nitrobenzyl, p-methoxybenzyl, phenacyl and diphenylmethyl, an organic silyl group for example trimethylsilyl, an organic stannyl group for example trimethylstannyl, an organic phosphoryl group for example ethylene phosphoryl, and an organic boronyl group for example an ethylene boronyl group.

The α-amino group is usually reacted in its free form, but may be activated with an organic silyl group such as a trimethylsilyl group, an organic phosphoryl group such as an ethylene phosphoryl group or an organic boronyl group such as an ethylene boronyl group.

The reactive derivative of the formula (VIII) to be used includes those which are known to be useful for amide bond formation in the field of peptide, penicillin and cephalosporin chemistry such as an acid halide, for example an acid chloride and acid bromide, an acid azide, an acid anhydride, a mixed acid anhydride with an aryl sulfonic acid, an alkyl carbonate, an alkyl phosphate and aliphatic carboxylic acid, an active ester such as a p-nitrophenyl ester, a p-nitrophenyl thioester and a N-hydroxysuccinimide ester, and an acid amide with imidazole, dimethylpyrazole or triazole.

Exemplary of the heterocyclic Ar groups are furyl, thienyl, and pyridyl.

In the case where the free carboxylic acid of the formula (VII) is used, a condensing agent may be used, such as a N,N'-dicyclohexylcarbodiimide, an isoxazolium salt, a pyridinium salt or a diphenyl phosphoroazidate which have been widely used in peptide bond formation.

The reaction is conducted in an aqueous organic solvent which does not inhibit the reaction. Particularly preferable are tetrahydrofuran, acetone, dioxane, dimethylformamide, dimethylacetamide, dichloromethane, chloroform, dimethylsulfoxide, isobutyl ketone and benzene. The reaction is conducted at a temperature ranging from about −50° to +50° C., preferably from −20° C. to room temperature.

When the acid is liberated during the course of reaction, it is preferable to use an inorganic base such as an alkali hydrogen carbonate or an alkali carbonate, or a tertiary organic base such as triethylamine, pyridine, picoline, N-methylpiperazine or dimethylaniline.

The present compounds possess excellent antibacterial activity and are useful for the treatment of bacterially caused diseases. The antibacterial activities of these compounds are shown below.

Minimum growth inhibition concentration (MIC) (μg/ml)

| Compound | Bacteria A | B | C | D | E |
|---|---|---|---|---|---|
| 1 | 0.10 | 0.78 | 1.56 | 1.56 | 3.13 |
| 2 | 0.10 | 0.78 | 1.56 | 1.56 | 6.25 |
| 3 | 0.05 | 0.20 | 0.78 | 0.78 | 6.25 |
| 4 | 0.05 | 0.78 | 3.13 | 3.13 | 12.5 |
| 5 | 0.025 | 0.10 | 0.78 | 0.39 | 3.13 |
| 6 | 0.10 | 0.78 | 0.78 | 1.56 | 6.25 |
| 7 | 0.10 | 0.20 | 1.56 | 3.13 | 6.25 |
| 8 | 0.05 | 0.39 | 0.78 | 1.56 | 3.13 |
| 9 | 0.05 | 0.78 | 0.39 | 1.56 | 6.25 |
| 10 | 0.10 | 0.39 | 0.78 | 1.56 | 3.13 |
| 11 | 0.05 | 0.39 | 0.39 | 1.56 | 6.25 |
| 12 | 0.05 | 0.78 | 0.78 | 1.56 | 12.5 |
| 13 | 0.025 | 0.78 | 0.78 | 1.56 | 6.25 |
| 14 | 0.10 | 0.10 | 6.25 | 6.25 | 6.25 |
| 15 | 0.10 | 0.20 | 3.13 | 1.56 | 6.25 |
| 16 | 0.10 | 0.20 | 6.25 | 1.56 | 6.25 |
| 17 | 0.05 | 0.39 | 1.56 | 1.56 | 6.25 |
| 18 | 0.10 | 0.78 | 6.25 | 0.78 | 6.25 |
| Amoxycillin | 0.05 | 1.56 | 50 | 1.56 | 100 |

$10^6$ cells/ml

Bacteria:
A:*Staphylococcus aureus* ATCC6538P
B:*Escherichia coli* NIHJ
C:*Proteus vulgaris* ATCC6897
D:*Klebsiella pneumoniae* ATCC10031
E:*Pseudomonas aeruginosa* IFO3080

Compounds:

1: D(−)-α-(chalcone-4-carboxamido)benzylpenicillin potassium salt
2: D(−)-α-(chalcone-4-carboxamido)p-hydroxy benzylpenicillin potassium salt
3: D(−)-α-(chalcone-4'-carboxamido)benzylpenicillin sodium salt
4: D(−)-α-(chalcone-4'-carboxamido)p-hydroxy benzylpenicillin sodium salt
5: D(−)-α-(p-styrylbenzamido)benzylpenicillin sodium salt
6: D(−)-α-(p-styrylbenzamido)p-hydroxy benzylpenicillin sodium salt
7: D(−)-α-(4'-methoxychalcone-4-carboxamido) benzylpenicillin sodium salt
8: D(−)-α-(2-chlorochalcone-4'-carboxamido) benzylpenicillin sodium salt
9: D(−)-α-(4-chlorochalcone-4'-carboxamido) benzylpenicillin sodium salt
10: D(−)-α-(4-chlorochalcone-4'-carboxamido) p-hydroxybenzylpenicillin sodium salt
11: D(−)-α-[p-(5-phenylpenta-2,4-dienoyl)benzamido] benzylpenicillin sodium salt
12: D(−)-α-[p-(5-phenylpenta-2,4-dienoyl)benzamido] p-hydroxybenzylpenicillin sodium salt
13: D(−)-α-[p-[β-(2-thienyl)acryloyl]benzamido] benzylpenicillin sodium salt
14: D(−)-α-[p-[β-(2-pyridyl)acryloyl]benzamido] benzylpenicillin sodium salt
15: D(−)-α-(6-styrylnicotinamido)benzylpenicillin sodium salt
16: D(−)-α-[6-(2-thien-2-ylethenyl)nicotinamido]p-hydroxybenzylpenicillin sodium salt
17: D(−)-α-[p-(4-phenlbuta-1,3-dienyl)benzamido]p-hydroxybenzylpenicillin sodium salt
18: D(−)-α-[6-(4-phenylbuta-1,3-dienyl)nicotinamido] benzylpenicillin sodium salt As can be seen from the above results, the present compounds exert an excellent effect against Pseudomonas aeruginosa in comparison with Amoxycillin which is a well-known antibiotic drug and has been widely used in the world.

The present componds and non-toxic salts thereof may be used as medicaments in human medicine in the form of pharmaceutical compositions These compounds can be administered by a parenteral route such as intravenous and intramuscular injection, or by an oral route in the form of tablets, powder, capsules, and syrup. Usually the compounds are administered in single or divided doses of about 150 mg to 3,000 mg per adult per day, depending on the diseases, age, body weight and medication route.

This invention is illustrated below in further detail with reference to several Examples, but the invention is not limited to these Examples.

EXAMPLE 1

D(−)-α-(chalcone-4-carboxamido)-benzyl penicillin potassium salt: A mixture of 252 mg of chalcone-4-carboxylic acid, a drop of dimethylformamide and 1.5 ml of oxalyl chloride was stirred for 1 hour at room temperature and concentrated to dryness under reduced pressure. To 350 mg of α-aminobenzyl penicillin trihydrate were added 10 ml of an aqueous solution containing 80% tetrahydrofuran and then triethylamine to adjust the pH of the solution to a range of 8.0 to 8.5. To this solution was added dropwise with stirring and with ice-cooling the above-mentioned chalcone-4-carboxylic acid chloride dissolved in 5 ml of tetrahydrofuran. During the course of addition, the pH of the solution was kept within a range of 7.5 to 8.0 by adding triethylamine. After the addition, the mixture was stirred with ice-cooling for 1 hour. Tetrahydrofuran was evaporated under reduced pressure at room temperature to obtain a residue, which was dissolved by adding 30 ml of water. The solution was washed twice with ethyl acetate. Ethyl acetate was added to the aqueous solution, and the pH was adjusted to 1.5 with hydrochloric acid.

An ethyl acetate layer was collected, washed twice with water and dried oer anhydrous sodium sulfate. The solvent was evaporated under reduced pressure. The residue was dissolved in acetone, and to the resulting solution were added 2 ml of a solution containing acetone and 200 mg of a 2-ethyl-hexanoic acid potassium salt and then ehter to separate white crystals which were collected, and there was obtained 440 mg (yield: 82%) of a D(−)-α-(chalcone-4-carboxamido)-benzyl penicillin potassium salt having a melting point of 180° to 190° C. (decomposition). $[\alpha]_D^{20} = +120°$ IR$\nu_{max}^{KBr}$ cm$^{-1}$: 1760, 1660(sh), 1640(sh), 1600

NMR (DMSO-d$_6$) δ:
1.40 (3H, s, C$_{2\alpha}$-CH$_3$)
1.50 (3H, s, C$_{2\beta}$-CH$_3$)
3.82 (1H, s, C$_3$—CH)

5.4 (2H, m's, C$_5$—CH and C$_6$—CH)
5.88 (1H, d,

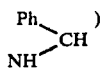

7.2–8.2 (16H, m's, aromatic and olefinic protons)
8.6–9.0 (2H, m's, NH's)

EXAMPLE 2

D(−)-Δ-(chalcone-4-carboxamido)-p-hydroxy benzyl penicillin potassium salt:

A mixture of 252 mg of chalcone-4-carboxylic acid, a drop of dimethylformamide and 1.5 ml of oxalyl chloride was stirred for 1 hour at room temperature and concentrated to dryness under reduced pressure. To 420 mg of α-amino-p-hydroxy benzyl penicillin trihydrate were added 10 ml of an aqueous solution containing 80% tetrahydrofuran and then triethylamine to adjust the pH of the solution to a range of 8.0 to 8.5. To this solution was added dropwise with stirring and with ice-cooling the above-mentioned chalcone-4-carboxylic acid chloride dissolved in 5 ml of tetrahydrofuran. During the course of addition, the mixture was stirred with ice-cooling for 1 hour. Terahydrofuran was evaporated under reduced pressure at room temperature to obtain the residue, which was dissolved by adding 30 ml of water. The solution was washed twice with ethyl acetate. To the aqueous solution was added ethyl acetate and the pH was adjusted to 1.5 with hydrochloric acid.

An ethyl acetate layer was collected, washed twice with water and dried over anhydrous sodium sulfate. The solvent was evaporated under reduced pressure. The residue was dissolved in acetone and to the resulting solution were added 2 ml of a solution containing acetone and 200 mg of 2-ethyl-hexanoic acid potassium salt and then ether to separate white crystals which were collected, and there was obtained 533 mg (yield: 84%) of a D(−)-α-(chalcone-4-carboxamido)-p-hydroxy benzyl penicillin potassium salt having a melting point of 200°–210° C. (decomposition).

[α]$_D^{20}$ = +128°
IR$\nu_{max}^{KBr}$ cm$^{-1}$: 1760, 1660 (sh), 1640(sh), 1600
NMR(DMSO-d$_6$) δ:
1.42 (3H, s, C$_{2\alpha}$—CH$_3$)
1.50 (3H, s, C$_{2\beta}$—CH$_3$)
3.84 (1H, s, C$_3$—CH)
5.4 (2H, m's, C$_5$—CH and C$_6$—CH)
5.76 (1H, d,

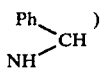

6.72 (2H, d, aromatic protons)
7.26 (2H, d, aromatic protons)
7.5–8.2 (11H, m's, aromatic and olefinic protons)
8.6–8.9 (2H, m's, NH's)

EXAMPLE 3

D(−)-α-(chalcone-4'-carboxamido)-benzyl penicillin sodium salt:

A mixture of 252 mg of chalcone-4'-carboxylic acid, a drop of dimethylformamide and 1.5 ml of oxalyl chloride was stirred under a dry atmosphere for 1 hour at room temperature and concentrated to dryness under reduced pressure at room temperature. 404 mg of α-aminobenzyl penicillin trihydrate was suspended in 10 ml of an aqueous solution containing 80% tetrahydrofuran, and to the resulting mixture was added triethylamine to adjust the pH of the solution to a range of 8.0 to 8.5. To this solution was added dropwise with stirring and with ice-cooling the above mentioned chalcone-4'-carboxylic acid chloride dissolved in 5 ml of tetrahydrofuran. After the addition, the mixture was stirred with ice-cooling for 1 hour. During the course of addition and thereafter, the pH of the solution was kept within a range of 7.5 to 8.0 by adding triethylamine. Tetrahydrofuran was evaporated under reduced pressure at room temperature to obtain a residue. To this residue were added 30 ml of water and a sodium hydrogencarbonate solution to adjust the pH of the solution to 9, and the solution was washed with 20 ml of ethyl acetate. To the aqueous solution was added 30 ml of ethyl acetate, and the pH was adjusted to 1.5 with ice-cooling with 10% hydrochloric acid.

An ethyl acetate layer was collected, washed twice with a portion of 20 ml of water and dried over anhydrous sodium sulfate. The solvent was evaporated under reduced pressure. The residue dissolved in 2 ml of acetone, and to the resulting solution were added 2 ml of a solution containing ethyl acetate and 200 mg of a 2-ethyl-hexanoic acid sodium salt and then 30 ml of ether to separate white precipitates which were collected by filtration and washed with ether, and there was obtained 434 mg (yield: 72%) of a D(−)-α-(chalcone-4'-carboxamido)benzyl penicillin sodium salt as a white powder having a melting point of 190° to 220° C. (decomposition).

[α]$_D^{20}$ = +201°
IR$\nu_{max}^{KBr}$ cm$^{-1}$: 1760, 1640, 1590
NMR(DMSO-d$_6$) δ:
1.42 (3H, s, C$_{2\alpha}$—CH$_3$)
1.50 (3H, s, C$_{2\beta}$—CH$_3$)
3.98 (1H, s, C$_3$—CH)
5.4 (2H, m's, C$_5$-CH and C$_6$-CH)
5.98 (1H, d,

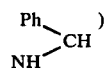

7.2–8.3 (16H, m's, aromatic and olefinic protons)
8.98 (1H, d, NH)
9.14 (1H, d, NH)

EXAMPLE 4

D(−)-α-(chalcone-4'-carboxamido)-p-hydroxybenzyl penicillin sodium salt:

A mixture of 252 mg of chalcone-4'-carboxylic acid, a drop of dimethylformamide and 1.5 ml of oxalyl chloride was stirred under a dry atmosphere for 1 hour at room temperature and concentrated to dryness under reduced pressure at room temperature. 420 mg of α-amino-p-hydroxybenzylpenicillin trihydrate was suspended in 10 ml of an aqueous solution containing 80% tetrahydrofuran, and to the resulting mixture was added triethylamine to adjust the pH of the solution to a range of 8.0 to 8.5. To this solution was added dropwise with stirring and with ice-cooling the above-mentioned chalcone-4'-carboxylic acid chloride dissolved in 5 ml of tetrahydrofuran. After the addition, the mixture was stirred with ice-cooling for 1 hour. During the course of addition and thereafter, the pH of the solution was kept within a range of 7.5 to 8.0 by adding triethylamine.

Tetrahydrofuran was evaporated under reduced pressure at room temperature to obtain a residue. To this residue were added 30 ml of water and a sodium hydrogencarbonate solution to adjust the pH of the solution to 9. The solution was washed with 20 ml of ethyl acetate. To the aqueous solution was added 30 ml of ethyl acetate, and the pH was adjusted to 1.5 with 10% hydrochloric acid.

An ethyl acetate layer was collected, washed twice with a portion of water and dried over anhydrous sodium sulfate. The solvent was evaporated under reduced pressure. The residue was dissolved in 2 ml of acetone, and to the resulting solution were added 2 ml of a solution containing ethyl acetate and 200 mg of a 2-ethyl-hexanoic acid sodium salt and then 30 ml of ether to separate white precipitates which were collected by filtration and washed with ether, and there was obtained 600 mg (yield: 96%) of a D(−)-α-(chalcone-4′-carboxamido)p-hydroxybenzylpenicillin sodium salt as a white powder having a melting point of 205°–240° C. (decomposition).

$[\alpha]_D^{20} = +127°$
IR$\nu_{max}^{KBr}$ cm$^{-1}$: 1760, 1660 (sh), 1640 (sh), 1590
NMR(DMSO—d$_6$) δ:
1.44 (3H, s, C$_2$—CH$_3$)
1.52 (3H, s, C$_2$—CH$_3$)
3.86 (1H, s, C$_3$—CH)
5.34 (2H, m's, C$_5$—CH and C$_6$—CH)
5.74 (1H, d,

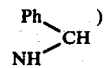

6.68 (2H, d, aromatic protons)
7.22 (2H, d, aromatic protons)
7.3—8.2 (11H, m's, aromatic and olefinic protons)
8.66 (1H, d, NH)
8.88 (1H, d, NH)

EXAMPLE 5

D(−)-α-(p-styrylbenzamido)-benzyl pencillin sodium salt:

A mixture of 224 mg of p-styrylbenzoic acid, a drop of dimethylformamide, 5 ml of dry tetrahydrofuran and 0.17 ml of oxalyl chloride was stirred with ice-cooling under a dry atmosphere for 30 minutes. To an aqueous solution containing 80% tetrahydrofuran were added 404 mg of α-aminobenzyl penicillin trihydrate and triethylamine to adjust the pH of the solution to a range of 8.0 to 8.5. To this solution was added dropwise with stirring and ice-cooling the above-mentioned p-stylylbenzoic acid chloride solution. During the course of addition, the pH of the solution was kept within a range of 7.5 to 8.0 by adding triethylamine. One hour after the completion of addition, tetrahydrofuran was evaporated under reduced pressure at room temperature to obtain a residue. To this residue were added water and a sodium hydrogencarbonate solution to adjust the pH of the solution to about 8. The solution was washed with ethyl acetate. To the aqueous solution was then added ethyl acetate, and the pH was adjusted to 1.5 with stirring and ice-cooling by 10% hydrochloric acid.

An ethyl acetate layer was collected, washed with water and dried over anhydrous sodium sulfate. Ethyl acetate was evaporated under reduced pressure at room temperature. The residue was dissolved in about 5 ml of acetone, and to the resulting solution were added 2 ml of a solution containing ethyl acetate and 200 mg of a 2-ethyl-hexanoic acid sodium salt and then ether to separate precipitates which were collected by filtration, and there was obtained 527 mg (yield: 91%) of a D(−)-α(p-styrylbenzamide)-benzyl penicillin sodium salt as a white powder.

$[\alpha]_D^{25} = 140°$ 0.5(g/ml)% methanol solution
IR $\nu_{max}^{KBr}$ cm$^{-1}$: 1760, 1610
NMR(DMSO-d$_6$)δ:
1.44 (3H, s, C$_{2\alpha}$—CH$_3$)
1.54 (3H, s, C$_{2\beta}$—CH$_3$)
3.88 (1 H, s, C$_3$—CH)
5.4 (2H, m's, C$_5$—CH and C$_6$—CH)
5.92 (1H, d,

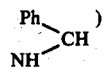

7.2–7.9 (16H, m's, aromatic and olefinic protons)
8.86 (2H, d's, NH)

EXAMPLE 6

D(−)-α-(p-styrylbenzamido)p-hydroxybenzyl penicillin sodium salt:

The same procedure was repeated as in Example 5 with the exception that 224 mg of p-styrylbenzoic acid and 420 mg of α-amino-p-hydroxybenzyl penicillin trihydrate were used, and there was obtained 518 mg (yield: 87%) of a D(−)-α-(p-styrylbenzamido)p-hydroxybenzyl penicillin sodium salt as a white powder.

$[\alpha]_D^{25} + 112°$ 0.5(g/ml)% methanol solution
IR $\nu_{max}^{KBr}$ cm$^{-1}$: 1760, 1610
NMR(DMSO-d$_6$)δ:
1.44 (3H, s, C$_{2\alpha}$—CH$_3$)
1.52 (3H, s, C$_{2\beta}$—CH$_3$)
3.86 (1H, s, C$_3$—CH)
5.3 (2H, m's, C$_5$—CH and C$_6$—CH)
5.72 (1H, d,

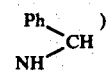

6.66 (2H, d, aromatic protons)
7.1–7.9 (13H, m's, aromatic and olefinic protons)
8.62 (2H, d's, NH's)

EXAMPLE 7

D(−)-α-(4′-methoxychalcone-4-carboxamido)benzyl penicillin sodium salt:

The same procedure was repeated as in Example 5 with the exception that 282 mg of 4′-methoxychalcone-4-carboxylic acid and 404 mg of α-aminobenzylpenicillin trihydrate were used and there was obtained 531 mg (yield: 83%) of a D(−)-α-(4′-methoxychalcone-4-carboxamide)benzylpenicillin sodium salt as a white powder.

$[\alpha]_D^{25} + 128°$ 0.5(g/ml)% methanol solution
IR $\nu_{max}^{KBr}$ cm$^{-1}$: 1760, 1660(sh), 1640(sh), 1600
NMR(DMSO-d$_6$)δ:
1.42 (3H, s, C$_{2\alpha}$—CH$_3$)
1.50 (3H, s, C$_{2\beta}$—CH$_3$)
3.8 (1H, s, C$_3$—CH)
3.84 (3H, s, OCH$_3$)
5.3 (2H, m, C$_5$—CH and C$_6$—CH)
5.92 L (1H, d,

7.0–8.1 (15H, m, aromatic and olefinic protons)
8.9 (2H, d, NH)

EXAMPLE 8

D(—)-α-(4'-methoxychalcone-4-carboxamido)p-hydroxy benzyl penicillin sodium salt:

The same procedure was repeated as in Example 5 with the exception that 282 mg of 4'-methoxychalcone-4-carboxylic acid and 420 mg of α-amino-p-hydroxybenzyl penicillin trihydrate were used, and there was obtained 476 mg (yield: 73%) of a D(—)-α-(4'-methoxychalcone-4-carboxamide)-p-hydroxybenzyl penicillin sodium salt as a white powder.

$[\alpha]_D^{25} + 109°$ 0.5(g/ml)% methanol solution
IR $\nu_{max}^{KBr}$ cm$^{-1}$: 1760, 1660(sh), 1640(sh), 1600
NMR(DMSO-d$_6$)δ:
1.44 (3H, s, C$_{2\alpha}$—CH$_3$)
1.54 (3H, s, C$_{2\beta}$—CH$_3$)
3.88 (3H, s, OCH$_3$)
3.92 (1H, s, C$_3$—CH)
5.4 (2H, m's, C$_5$—CH and C$_6$—CH)
5.80 (1H, d,

6.78 (2H, d, aromatic protons)
7.10 (2H, d, aromatic protons)
7.32 (2H, d, aromatic protons)
7.74 (1H, d, olefinic proton)
8.00 (4H, s, aromatic protons)
about 8.00 (1H, d, olefinic proton)
8.20 (2H, d, aromatic protons)
8.8 (2H, d's, NH)

EXAMPLE 9

D(—)-α-(2-chlorochalcone-4'-carboxamido)benzyl penicillin sodium salt:

The same procedure was repeated as in Example 5 with the exception that 286.5 mg of 2-chlorochalcone-4'-carboxylic acid and 404 mg of α-aminobenzyl penicillin trihydrate were used, and there was obtained 529 mg (yield: 83%) of a D(—)-α-(2-chlorochalcone-4'-carboxamido)benzyl penicillin sodium salt as a white powder.

$[\alpha]_D^{25} + 118°$
IR $\nu_{max}^{KBr}$ cm$^{-1}$: 1760, 1660(sh), 1640(sh), 1600
NMR(DMSO-d$_6$)δ:
1.38 (3H, s, C$_{2\alpha}$—CH$_3$)
1.48 (3H, s, C$_{2\beta}$—CH$_3$)
3.86 (1H, s, C$_3$—CH)
5.4 (2H, m's, C$_5$—CH and C$_6$—CH)
5.96 (1H, d,

7.2–7.6 (8H, m's, aromatic and olefinic protons)
8.0–8.3 (7H, m's, aromatic and olefinic protons)
8.96 (1H, d, NH)
9.26 (1H, d, NH)

EXAMPLE 10

D(—)-α-(2-chlorochalcone-4'-carboxamido)p-hydroxybenzylpenicillin sodium salt:

The same procedure was repeated as in Example 5 with the exception that 286.5 mg of 2-chlorochalcone-4'-carboxylic acid and 420 mg of α-amino-p-hydroxybenzyl penicillin trihydrate were used, and there was obtained 582 mg (yield: 89%) of a D(—)-α-(2-chlorochalcone-4'-carboxamido)p-hydroxybenzylpenicillin sodium salt as a white powder.

$[\alpha]_D^{25} + 101°$
IR $\nu_{max}^{KBr}$ cm$^{-1}$: 1760, 1660(sh), 1640(sh), 1600
NMR(DMSO-d$_6$)δ:
1.44 (3H, s, C$_{2\alpha}$—CH$_3$)
1.52 (3H, s, C$_{2\beta}$—CH$_3$)
3.88 (1H, s, C$_3$—CH)
5.4 (2H, m's, C$_5$—CH and C$_6$—CH)
5.76 (1H, d,

6.68 (2H, d, aromatic protons)
7.22 (2H, d, aromatic protons)
7.3–7.5 (3H, m's, aromatic and olefinic protons)
7.9–8.2 (7H, m's, aromatic and olefinic protons)
8.68 (1H, d, NH)
8.90 (1H, d, NH)

EXAMPLE 11

D(—)-α-(4-chlorochalcone-4'-carboxamido)benzylpenicillin sodium salt:

The same procedure was repeated as in Example 5 with the exception that 286.5 mg of 4-chlorochalcone-4'-carboxylic acid and 404 mg of α-aminobenzylpenicillin trihydrate were used, and there was obtained 523 mg (yield: 82%) of a D(—)-α-(4-chlorochalcone-4'-carboxamido)benzylpenicillin sodium salt as a white powder.

$[\alpha]_D^{25} + 101°$
IR $\nu_{max}^{KBr}$ cm$^{-1}$: 1760, 1660(sh), 1590
NMR(DMSO-d$_6$)δ:
1.40 (3H, s, C$_{2\alpha}$—CH$_3$)
1.50 (3H, s, C$_{2\beta}$—CH$_3$)
3.86 (1H, s, C$_3$—CH)
5.34 (2H, m's, C$_5$—CH and C$_6$—CH)
5.94 (1H, d,

7.2–8.2 (15H, m's, aromatic and olefinic protons)
8.92 (1H, d, NH)
9.12 (1H, d, NH)

EXAMPLE 12

D(—)-α-(4-chlorochalcone-4'-carboxamido)p-hydroxybenzylpenicillin sodium salt:

The same procedure was repeated as in Example 5 with the exception that 286.5 mg of 4-chlorochalcone-4'-carboxylic acid and 420 mg of α-amino-p-hydroxybenzylpenicillin trihydrate were used, and there was obtained 623 mg (yield: 95%) of a D(—)-α-(4-chlorochalcone-4'-carboxamide)p-hydroxybenzylpenicillin sodium salt as a white powder.

$[\alpha]_D^{25} + 101°$

IR $\nu_{max}^{KBr}$ cm$^{-1}$: 1760, 1660(sh), 1640(sh), 1600
NMR(DMSO-d$_6$)δ:
1.44 (3H, s, C$_{2\alpha}$—CH$_3$)
1.54 (3H, s, C$_{2\beta}$—CH$_3$)
3.88 (1H, s, C$_3$—CH)
5.33 (2H, m's, C$_5$—CH and C$_6$—CH)
5.74 (1H, d,

6.68 (2H, d, aromatic protons)
7.20 (2H, d, aromatic protons)
7.4–8.2 (10H, m's, aromatic and olefinic protons)
8.66 (1H, d, NH)
8.86 (1H, d, NH)

EXAMPLE 13

D(−)-α-[p-(5-phenylpenta-2,4-dienoyl)benzamido]-benzylpenicillin sodium salt:

The same procedure was repeated as in Example 5 with the exception that 278 mg of p-(5-phenylpenta-2,4-dienoyl)benzoic acid and 404 mg of α-aminobenzylpenicillin trihydrate were used, and there was obtained 533 mg (yield: 84%) of a D(−)-α-[p-(5-phenylpenta-2,4-dienoyl)benzamido]-benzylpenicillin sodium salt as a yellow powder.

$[\alpha]_D^{25}$ +107°
IR $\nu_{max}^{KBr}$ cm$^{-1}$: 1760, 1660(sh), 1640(sh), 1600, 1580
NMR(DMSO-d$_6$)δ:
1.40 (3H, s, C$_{2\alpha}$—CH$_3$)
1.50 (3H, s, C$_{2\beta}$—CH$_3$)
3.88 (1H, s, C$_3$—CH)
5.44 (2H, m's, C$_5$—CH and C$_6$—CH)
5.94 (1H, d,

7.2–7.6 (14H, m's, aromatic and olefinic protons)
8.06 (4H, s, aromatic protons)
8.92 (1H, d, NH)
9.10 (1H, d, NH)

EXAMPLE 14

D(−)-α-[p-(5-phenylpenta-2,4-dienoyl)benzamido]p-hydroxybenzylpenicillin sodium salt:

The same procedure was repeated as in Example 5 with the exception that 278 mg of p-(5-phenylpenta-2,4-dienoyl)benzoic acid and 420 mg of α-amino-p-hydroxybenzylpenicillin trihydrate were used and there was obtained 527 mg (yield: 81%) of a D(−)-α-[p-5-phenylpenta-2,4-dienoyl)benzamido]p-hydroxybenzylpenicillin sodium salt as a yellow powder.

$[\alpha]_D^{25}$ +117°
IR $\nu_{max}^{KBr}$ cm$^{-1}$: 1760, 1660(sh), 1640(sh), 1600, 1580
NMR(DMSO-d$_6$)δ:
1.42 (3H, s, C$_{2\alpha}$—CH$_3$)
1.52 (3H, s, C$_{2\beta}$—CH$_3$)
3.88 (1H, s, C$_3$—CH)
5.4 (2H, m's, C$_5$—CH and C$_6$—CH)
5.78 (1H, d,

6.72 (2H, d, aromatic protons)
7.2–7.7 (11H, m's, aromatic and olefinic protons)
8.04 (4H, s, aromatic protons)
8.72 (1H, d, NH)
8.94 (1H, d, NH)

EXAMPLE 15

D(−)-α-[p-[β-(2-furyl)acryloyl]benzamido]benzylpenicillin sodium salt:

The same procedure was repeated as in Example 5 with the exception that 242 mg of p-[β-(2-furyl)acryloyl]benzoic acid and 404 mg of α-aminobenzylpenicillin trihydrate were used, and there was obtained 534 mg (yield: 90%) of a D(−)-α-[β-(2-furyl)acryloyl]benzamido]benzylpenicillin sodium salt as a pale yellow powder.

$[\alpha]_D^{25}$ +123°
IR $\nu_{max}^{KBr}$ cm$^{-1}$: 1760, 1660(sh), 1600
NMR(DMSO-d$_6$)δ:
1.40 (3H, s, C$_{2\alpha}$—CH$_3$)
1.50 (3H, s, C$_{2\beta}$—CH$_3$)
3.88 (1H, s, C$_3$—CH)
5.4 (2H, m's, C$_5$—CH and C$_6$—CH)
5.94 (1H, d,

6.64 (1H, dd, aromatic proton)
7.1–8.1 (13H, m's, aromatic and olefinic protons)
8.90 (1H, d, NH)
9.10 (1H, d, NH)

EXAMPLE 16

D(−)-α-[p-[β-(2-furyl)acryloyl]benzamido]p-hydroxybenzylpenicillin sodium salt:

The same procedure was repeated as in Example 5 with the exception that 242 mg of p[β-(2-furyl)acryloyl]benzoic acid and 420 mg of α-amino-p-hydroxybenzylpenicillin trihydrate were used, and there was obtained 501 mg (yield: 82%) of a D(−)-α-[p-[β-(2-furyl)acryloyl]benzamido]p-hydroxybenzylpenicillin sodium salt as a pale yellow powder.

$[\alpha]_D^{25}$ +123°
IR $\nu_{max}^{KBr}$ cm$^{-1}$: 1760, 1660(sh), 1640(sh), 1600
NMR(DMSO-d$_6$)δ:
1.42 (3H, s, C$_{2\alpha}$—CH$_3$)
1.52 (3H, s, C$_{2\beta}$—CH$_3$)
3.88 (1H, s, C$_3$—CH)
5.4 (2H, m's, C$_5$—CH and C$_6$—CH)
5.78 (1H, d,

6.7 (3H, m's, aromatic protons)
7.10 (1H, d, aromatic proton)
7.28 (2H, d, aromatic protons)
7.54 (2H, s, olefinic protons)
7.9–8.1 (5H, m's, aromatic protons)
8.72 (1H, d, NH)

8.96 (1H, d, NH)

EXAMPLE 17

D(−)-α-[p-[β-(2-thienyl)acryloyl]benzamido]benzylpenicillin sodium salt:

The same procedure was repeated as in Example 5 with the exception that 258 mg of p-[β-(2-thienyl)acryloyl]-benzoic acid and 404 mg of α-aminobenzylpenicillin trihydrate were used, and there was obtained 551 mg (yield: 90%) of a D(−)-α-p-[β-(2-thienyl)acryloyl]benzamido]benzylpenicillin sodium salt as a pale yellow powder.

$[\alpha]_D^{25}+136°$

IR $\nu_{max}^{KBr}$ cm$^{-1}$: 1760, 1660(sh), 1640(sh), 1600(sh), 1590

NMR(DMSO-d$_6$)δ:
1.42 (3H, s, C$_{2\alpha}$—CH$_3$)
1.50 (3H, s, C$_{2\beta}$—CH$_3$)
3.88 (1H, s, C$_3$—CH)
5.4 (2H, m's, C$_5$—CH and C$_6$—CH)
5.96 (1H, d,

7.2-8.2 (14H, m's, aromatic and olefinic protons)
8.94 (1H, d, NH)
9.16 (1H, d, NH)

EXAMPLE 18

D(−)-α-[p-[β-(2-thienyl)acryloyl]benzamido]p-hydroxybenzylpenicillin sodium salt:

The same procedure was repeated as in Example 5 with the exception that 258 mg of p-[β-(2-thienyl)acryloyl]benzoic acid and 420 mg of α-amino-p-hydroxybenzylpenicillin trihydrate were used, and there was obtained 530 mg (yield: 84%) of a D(−)-[p-[β-(2-thienyl)acryloyl]benzamido]p-hydroxybenzylpenicillin sodium salt as a pale yellow powder.

$[\alpha]_D^{25}+116°$

IR $\nu_{max}^{KBr}$ cm$^{-1}$: 1760, 1660(sh), 1640(sh), 1600(sh), 1590

NMR(DMSO-d$_6$)δ:
1.42 (3H, s, C$_{2\alpha}$—CH$_3$)
1.50 (3H, s, C$_{2\beta}$—CH$_3$)
3.88 (1H s, C$_3$—CH)
5.4 (2H, m's, C$_5$—CH and C$_6$—CH)
5.80 (1H, d,

6.76 (2H, d, aromatic protons)
7.2-8.2 (11H, m's, aromatic and olefinic protons)
8.78 (1H, d, NH)
9.00 (1H, d, NH)

EXAMPLE 19

D(−)-α-[p-[3-(2-thienyl)prop-1-ene-3-onyl]benzamido]benzylpenicillin sodium salt:

The same procedure was repeated as in Example 5 with the exception that 258 mg of p-[3-(2-thienyl)-prop-1-ene-3-onyl]benzoic acid and 404 mg of α-aminobenzylpenicillin trihydrate were used, and there was obtaned 522 mg (yield: 85%) of a D(−)-α-[p-[3-(2-thienyl)prop-1-ene-3-onyl]-benzamido]benzyl penicillin sodium salt as a white powder.

$[\alpha]_D^{25}+133°$

IR $\nu_{max}^{KBr}$ cm$^{-1}$: 1760, 1640, 1600
NMR(DMSO-d$_6$)δ:
1.40 (3H, s, C$_{2\alpha}$—CH$_3$)
1.50 (3H, s, C$_{2\beta}$—CH$_3$)
3.86 (1H, s, C$_3$—CH)
5.4 (2H, m's, C$_5$—CH and C$_6$—CH)
5.92 (1H, d,

7.3-8.1 (13H, m's, aromatic and olefinic protons)
8.32 (1H, d, aromatic proton)
8.9 (2H, d's, NH's)

EXAMPLE 20

D(−)-α-[p-[3-(2-thienyl)prop-1-ene-3-onyl]benzamido]p-hydroxybenzylpenicillin sodium salt:

The same procedure was repeated as in Example 5 with the exception that 258 mg of p-[3-(2-thienyl)prop-1-ene-3-onyl]benzoic acid and 420 mg of α-amino-p-hydroxybenzylpenicillin trihydrate were used, and there was obtained 540 mg (yield: 86%) of a D(−)-α-[p-[3-(2-thienyl)prop-1-ene-3-onyl]benzamido]p-hydroxybenzylpenicillin sodium salt as a white powder.

$[\alpha]_D^{25}+120°$

IR $\nu_{max}^{KBr}$ cm$^{-1}$: 1760, 1640, 1600
NMR(DMSO-d$_6$)δ:
1.44 (3H, s, C$_{2\alpha}$—CH$_3$)
1.52 (3H, s, C$_{2\beta}$—CH$_3$)
3.90 (1H, s, C$_3$—CH)
5,4 (2H, m's, C$_5$—CH and C$_6$—CH)
5.78 (1H, d,

6.74 (2H, d, aromatic protons) pl 7.28 (3H, m's, aromatic protons)
7.6-8.1 (9H, m's, aromatic and olefinic protons)
8.34 (1H, d, aromatic proton)
8.8 (2H, d's, NH's)

EXAMPLE 21

D(−)-α-[p-[β-(2-pyridyl)acryloyl]benzamido]benzylpenicillin sodium salt:

The same procedure was repeated as in Example 5 with the exception that 253 mg of p-[β-(2-pyridyl)acryloyl]-benzoic acid and 404 mg of α-aminobenzylpenicillin trihydrate were used, and there was obtained 404 mg (yield: 74%) of a D(−)-α-[p-[β-(2-pyridyl)acryloyl]benzamido]benzylpenicillin sodium salt as a pale yellow powder.

$[\alpha]_D^{25}+108°$

IR $\nu_{max}^{KBr}$ cm$^{-1}$: 1760, 1660(sh), 1640(sh), 1600
NMR(DMSO-d$_6$):
1.40 (3H, s, C$_{2\alpha}$—CH$_3$)
1.50 (3H, s, C$_{2\beta}$—CH$_3$)
3.88 (1H, s, C$_3$—CH)
5.4 (2H, m's, C$_5$—CH and C$_6$—CH)
5.98 (1H, d,

7.3–8.3 (14H m's, aromatic and olefinic protons)
8.72 (1H, m, aromatic proton)
8.96 (1H, d, NH)
9.18 (1H, d, NH)

EXAMPLE 22

D(−)-α-(6-styrylnicotinamido)-benzylpenicillin sodium salt:

The same procedure was repeated as in Example 5 with the exception that 225 mg of 6-styrylnicotinic acid and 404 mg of α-aminobenzylpenicillin trihydrate were used, and there was obtained 458 mg (yield: 79%) of a D(−)-α-(6-styrylnicotinamido)benzylpenicillin sodium salt as a pale yellow powder.

$[\alpha]_D^{25} + 127°$
IR $\nu_{max}^{KBr}$ cm$^{-1}$: 1760, 1650(sh), 1630(sh), 1590
NMR(DMSO-d$_6$)δ:
1.42 (3H, s, C$_{2\alpha}$—CH$_3$)
1.50 (3H, s, C$_{2\beta}$—CH$_3$)
3.92 (1H, s, C$_3$—CH)
5.4 (2H, m's, C$_5$—CH and C$_6$—CH)
6.00 (1H, d,

7.3–7.9 (13H, m's, aromatic and olefinic protons)
8.36 (1H, dd, aromatic proton)
9.14 (1H, d, aromatic proton)
9.1 (2H, d's, NH's)

EXAMPLE 23

D(−)-α-(6-styrylnicotinamido)p-hydroxybenzylpenicillin sodium salt:

The same procedure was repeated as in Example 5 with the exception that 225 mg of 6-styrylnicotinic acid and 420 mg of α-amino-p-hydroxybenzylpenicillin trihydrate were used, and there was obtained 503 mg (yield: 85%) of a D(−)-α-(6-styrylnicotinamido)p-hydroxybenzylpenicillin sodium salt as a white powder.

$[\alpha]_D^{25} + 126°$
IR $\nu_{max}^{KBr}$ cm$^{-1}$: 1760, 1640(sh), 1600
NMR(DMSO-d$_6$)δ:
1.42 (3H, s, C$_{2\alpha}$—CH$_3$)
1.52 (3H, s, C$_{2\beta}$—CH$_3$)
3.88 (1H, s, C$_3$—CH)
5.4 (2H, m's, C$_5$—CH and C$_6$—CH)
5.80 (1H, d,

6.74 (2H, d, aromatic protons)
7.2–7.9 (10H, m's, aromatic and olefinic protons)
8.26 (1H, dd, aromatic proton)
8.74 (1H, d, NH)
9.0 (1H, d, NH)
9.02 (1H, d, aromatic proton)

EXAMPLE 24

D(−)-α-(2'-hydroxychalcone-4-carboxamido)benzylpenicillin sodium salt:

The same procedure was repeated as in Example 5 with the exception that 268 mg of 2'-hydroxychalcone-4-carboxylic acid and α-aminobenzylpenicillin trihydrate were used, and there was obtained 501 mg (yield: 81%) of a D(−)-α-(2'-hydroxychalcone-4-carboxamido)benzylpenicillin sodium salt as a pale yellow powder.

IR $\nu_{max}^{KBr}$ cm$^{-1}$: 1770, 1660(sh), 1640, 1600
NMR(DMSO-d$_6$)δ:
1.40 (3H, s, C$_{2\alpha}$—CH$_3$)
1.50 (3H, s, C$_{2\beta}$—CH$_3$)
3.88 (1H, s, C$_3$—CH)
5.4 (2H, m's, C$_5$—CH and C$_6$—CH)
5.96 (1H, d,

6.9–8.2 (15H, m's, aromatic and olefinic protons)
9.0 (2H, d's, NH's)

EXAMPLE 25

D(−)-α-[p-(2-thien-2-ylethenyl)benzamido]benzylpenicillin sodium salt:

The same procedure was repeated as in Example 5 with the exception that 115 mg of p-(2-thien-2-ylethenyl)benzoic acid and 202 mg of α-aminobenzylpenicillin trihydrate were used, and there was obtained 215 mg (yield: 74%) of a D(−)-α-[p-(2-thien-2-ylethenyl)benzamido]benzylpenicillin sodium salt as a white powder.

$[\alpha]_D^{25} + 90°$
IR $\nu_{max}^{KBr}$ cm$^{-1}$: 1760, 1640(sh), 1600
NMR(DMSO-d$_6$)δ:
1.42 (3H, s, C$_{2\alpha}$—CH$_3$)
1.50 (3H, s, C$_{2\beta}$—CH$_3$)
3.92 (1H, s, C$_3$—CH)
5.4 (2H, m's C$_5$—CH and C$_6$—CH)
5.92 (1H, d,

6.9–8.0 (14H, m's, aromatic and olefinic protons)
8.9 (2H, d's, NH's)

EXAMPLE 26

D(−)-α-[p-(2-thien-2-ylethenyl)benzamido]p-hydroxybenzyl penicillin sodium salt:

The same procedure was repeated as in Example 5 with the exception that 115 mg of p-(2-thien-2-ylethenyl)benzoic acid and 210 mg of α-amino-p-hydroxybenzylpenicillin trihydrate were used, and there was obtained 190 mg (yield: 63%) of a D(−)-α-[p-(2-thien-2-ylethenyl)benzamido]p-hydroxybenzylpenicillin sodium salt as a white powder.

$[\alpha]_D^{25} + 116°$
IR $\nu_{max}^{KBr}$ cm$^{-1}$: 1760, 1660(sh), 1640(sh), 1600
NMR(DMSO-d$_6$)δ:
1.44 (3H, s, C$_{2\alpha}$—CH$_3$)
1.52 (3H, s, Chd 2$\beta$—CH$_3$)
3.86 (1H, s, C$_3$—CH)

5.3 (2H, m's, $C_5$—CH and $C_6$CH)
5.68 (1H, d,

6.6–7.8 (13H, m's, aromatic and olefinic protons)
8.56 (2H, d's, NH's)

EXAMPLE 27

D(—)-α-[6-(2-thien-2-ylethenyl)nicotinamido]benzylpenicillin sodium salt:

The same procedure was repeated as in Example 5 with the exception that 231 mg of 6-(2-thien-2-ylethenyl)nicotinic acid and 404 mg of α-aminobenzylpenicillin trihydrate were used, and there was obtained 450 mg of a D(—)-α-[6-(2-thien-2-ylethenyl)-nicotinamido]benzylpenicillin sodium salt as a pale yellow powder.

$[α]_D^{25} +117°$ IR $ν_{max}^{KBr}$ cm$^{-1}$: 1760, 1620(sh), 1590
NMR(DMSO-d$_6$) δ:
1.42 (3H, s, $C_{2α}$—CH$_3$)
1.52 (3H, s, $C_{2β}$—CH$_3$)
3.88 (1H, s, $C_3$—CH)
5.4 (2H, m's, $C_5$—CH and $C_6$—CH)
5.94 (1H, d,

7.0–8.2 (12H, m's, aromatic and olefinic protons)
8.92 (1H, d NH)
8.98 (1H, d, aromatic proton)
9.14 (1H, d, NH)

EXAMPLE 28

D(—)-α-[6-(2-thien-2-ylethenyl)nicotinamido]p-hydroxybenzyl penicillin sodium salt:

The same procedure was repeated as in Example 5 with the exception that 231 mg of 6-(2-thien-2-ylethenyl)nicotinic acid and 420 mg of α-amino-p-hydroxybenzylpenicillin trihydrate were used, and there was obtained 460 mg (yield: 77%) of a D(—)-α-[6-(2-thien-2-ylethenyl)nicotinamido]-p-hydroxybenzylpenicillin sodium salt as a white powder.

$[α]_D^{25} +119°$
IR $ν_{max}^{KBr}$ cm$^{-1}$: 1760, 1660(sh), 1620(sh), 1590
NMR(DMSO-d$_6$) δ:
1.42 (3H, s, $C_{2α}$—CH$_3$)
1.50 (3H, s, $C_{2β}$—CH$_3$)
3.88 (1H, s, $C_3$—CH)
5.4 (2H, m's, $C_5$—CH and $C_6$—CH)
5.78 (1H, d,

6.74 (2H, d, aromatic protons)
6.9–7.6 (7H, m's, aromatic and olefinic protons)
7.92 (1H, d, olefinic proton)
8.22 (1H, dd, aromatic proton)
8.74 (1H, d, NH)
8.96 (1H, d, NH)
9.98 (1H, d, aromatic proton)

EXAMPLE 29

D(—)-α-[p-(4-phenylbuta-1,3-dienyl)benzamido]benzylpenicillin sodium salt:

The same procedure was repeated as in Example 5 with the exception that 125 mg of p-(phenylbuta-1,3-dienyl)benzoic acid and 202 mg of α-aminobenzylpenicillin trihydrate were used, and there was obtained 246 mg (yield: 81%) of a D(—)-α-[p-(4-phenylbuta-1,3-dienyl)benzamido]-benzylpenicillin sodium salt as a pale yellow powder.

$[α]_D^{25} +135°$
IR $ν_{max}^{KBr}$ cm$^{-1}$: 1760, 1660(sh), 1640(sh), 1600
NMR(DMSO-d$_6$) δ:
1.40 (3H, s, $C_{2α}$—CH$_3$)
1.50 (3H, s, $C_{2β}$—CH$_3$)
3.86 (1H, s, $C_3$—CH)
5.4 (2H, m's, $C_5$—CH and $C_6$—CH)
5.92 (1H, d,

6.7–8.0 (18H, m's, aromatic and olefinic protons)
8.88 (2H, d's, NH's)

EXAMPLE 30

D(—)-α-[p-(4-phenylbuta-1,3-dienyl)benzamido]p-hydroxybenzylpenicillin sodium salt:

The same procedure was repeated as in Example 5 with the exception that 231 mg of p-(4-phenylbuta-1,3-dienyl)benzoic acid and 210 mg of α-amino-p-hydroxybenzylpenicillin trihydrate were used, and there was obtained 240 mg (yield: 77%) of a D(—)-α-[p-(4-phenylbuta-1,3-dienyl)benzamido]p-hydroxybenzylpenicillin sodium salt as a white powder.

$[α]_D^{25} +141°$
IR $ν_{max}^{KBr}$ cm$^{-1}$: 1760, 1640(sh), 1600
NMR(DMSO-d$_6$) δ:
1.42 (3H, s, $C_{2α}$—CH$_3$)
1.50 (3H, s, $C_{2β}$—CH$_3$)
3.90 (1H, s, $C_3$—CH)
5.4 (2H, m's, $C_5$—CH and $C_6$—CH)
5.76 (1H, d

6.7–8.0 (17H, m's, aromatic and olefinic protons)
8.70 (2H, d's, NH's)

EXAMPLE 31

D(—)-α-[6-(4-phenylbuta-1,3-dienyl)nicotinamido]-benzylpenicillin sodium salt:

The same procedure was repeated as in Example 5 with the exception that 126 mg of 6-(4-phenylbuta-1,3-dienyl)-nicotinic acid and 202 mg of α-aminobenzylpenicillin trihydrate were used, and there was obtained 232 mg (yield: 77%) of a D(—)-α-[6-(4-phenylbuta-1,3-dienyl)nicotinamido]-benzylpenicillin sodium salt as a pale yellow powder.

$[α]_D^{25} +127°$
IR $ν_{max}^{KBr}$ cm$^{-1}$: 1760, 1660(sh), 1640(sh), 1590
NMR(DMSO-d$_6$) δ:
1.40 (3H, s, $C_{2α}$—CH$_3$)
1.50 (3H, s, $C_{2β}$—CH$_3$)

3.88 (1H, s, $C_3$—CH)
5.4 (2H, m's, $C_5$—CH and $C_6$—CH)
5.94 (1H, d,

)

6.8–7.7 (15H, m's, aromatic and olefinic protons)
8.24 (1H, dd, aromatic proton)
8.92 (1H, d, NH)
9.00 (1H, d, aromatic proton)
9.14 (1H, d, NH)

EXAMPLE 32

D(—)-α-[6-(4-phenylbuta-1,3-dienyl)nicotinamido]p-hydroxybenzylpenicillin sodium salt:

The same procedure was repeated as in Example 5 with the exception that 126 mg of 6-(4-phenylbuta-1,3-dienyl)nicotinic acid and 210 mg of α-amino-p-hydroxybenzylpenicillin trihydrate were used, and there was obtained 232 mg (yield: 75%) of a D(—)-α-[6-(4-phenylbuta-1,3-dienyl)nicotinamido]p-hydroxybenzylpenicillin sodium salt as a white powder.

$[\alpha]_D^{25} + 130°$
IR $\nu_{max}^{KBr}$ cm$^{-1}$: 1760, 1640(sh), 1590
NMR(DMSO-$d_6$) δ:
1.42 (3H, s, $C_{2\alpha}$—$CH_3$)
1.52 (3H, s, $C_{2\beta}$—$CH_3$)
3.90 (1H, s, $C_3$—CH)
5.4 (2H, m's, $C_5$—CH and $C_6$—CH)
5.82 (1H, d,

)

6.8–7.7 (14H, m's, aromatic and olefinic protons)
8.22 (1H, dd, aromatic proton)
8.76 (1H, d, NH)
8.98 (1H, d, NH)
9.00 (1H, d, aromatic proton)

EXAMPLE 33

D(—)-7-[α-(chalcone-4-carboxamido)-phenylacetamido]cephalosporanic acid:

A mixture of 252 mg of chalocone-4-carboxylic acid, a drop of diemthylformamide, 5 ml of dry tetrahydrofuran and 0.17 ml of oxalyl chloride was stirred with ice-cooling under a dry atmosphere for 30 minutes. To an aqueous solution containing 80% tetrahydrofuran were added 406 mg of D-(—)-7-(α-aminophenylacetamido)cephalosporanic acid and triethylamine to adjust the ph of the solution to a range of 8.0 to 8.5. To this solution was added dropwise with stirring and ice-cooling the above-mentioned chalcone-4-carboxylic acid chloride solution. During the course of addition, the pH of the solution was kept within a range of 7.5 to 8.0 by adding triethylamine. One hour after the completion of dropping, tetrahydrofuran was evaporated under reduced pressure at room temperature to obtain a residue. To this residue were added water and a sodium hydrogencarbonate solution to adjust the pH of the solution to about 8. The solution was washed with ethyl acetate. To the aqueous solution was then added ethyl acetate, and the pH was adjusted to 1.5 with stirring and ice-cooling by 10% hydrochloric acid. An ethyl acetate layer was collected, washed with water and dried over anhydrous sodium sulfate. Ethyl acetate was evaporated under reduced pressure at room temperature, and there was obtained 140 mg (yield: 22%) of D(—)-7-[α-(chalcone-4-carboxamido)-phenylacetamido]cephalosporanic acid as a white powder.

IR $\nu_{max}^{KBr}$ cm$^{-1}$: 1780, 1730, 1660(sh), 1640
NMR(DMSO-$d_6$) δ:
2.02 (3H, s, $COCH_3$)
3.44 (2H, q, $C_2$—$CH_2$)
4.80 (2H, q, $C'_3$13 $CH_2$)
5.02 (1H, d, $C_6$—CH)
5.8 (2H, m's, $C_7$—CH and

)

7.3–8.2 (16H, m's, aromatic and olefinic protons)
8.92 (1H, d, NH)
9.24 (1H, d, NH)

EXAMPLE 34

D(—)-7-[α-(chalcone-4'-carboxamido)-phenylacetamido]cephalosporanic acid sodium salt:

The same procedure was repeated as in Example 5 with the exception that 252 mg of chalcone-4'-carboxylic acid and 406 mg of D(—)-7-(α-aminophenylacetamido)cephalosporanic acid were used, and there was obtained 527 mg (yield: 80%) of a D(—)-7-[α-(chalcone-4'-carboxmido)phenylacetamido]cephalosporanic acid sodium salt as a white powder.

IR $\nu_{max}^{KBr}$ cm$^{-1}$: 1760, 1660, 1600
NMR(DMSO-$d_6$) δ:
1.98 (3H, s, $COCH_3$)
3.24 (2H, q, $C_2$—$CH_2$)
4.86 (2H, q, $C'_3$—$CH_2$)
4.90 (1H, d, $C_6$—CH)
5.54 (1H, dd, $C_7$—CH)
5.90 (1H, d,

)

7.2–8.2 (16H, m's, aromatic and olefinic protons)
9.2 (2H, d's, NH's)

EXAMPLE 35

D(—)-7-[α-(p-styrylbenzamido)phenylacetamido]-cephalosporanic acid: The same procedure was repeated as in Example 33 with the exception that 224 mg of p-styrylbenzoic acid and 406 mg of D(—)-7-(α-aminophenylacetamido)cephalosporanic acid were used, and there was obtained 211 mg (yield: 34%) of D(—)-7-[α-(p-styrylbenzamido)phenylacetamido]cephalosporanic acid as a white powder.

IR $\nu_{max}^{KBr}$ cm$^{-1}$: 1780, 1720, 1630
NMR(DMSO-$d_6$) δ:
2.02 (3H, s, $COCH_3$)
3.44 (2H, broad s, $C_2$—$CH_2$)
4.80 (2H, q, $C_3'$—$CH_2$)
5.04 (1H, d, $C_6$—CH)
5.74 (1H, dd, $C_7$—CH)
5.88 (1H, d,

7.3-8.0 (16H, m's, aromatic and olefinic protons)
8.84 (1H, d, NH)
9.24 (1H, d, NH)

EXAMPLE 36

D(−)-7-[α-4′-methoxychalcone-4-carboxamido)-phenylacetamido]cephalosporanic acid sodium salt:

The same procedure was repeated as in Example 5 with the exception that 282 mg of 4′-methoxychalcone-4-carboxylic acid and 406 mg of D(−)-7-(α-aminophenylacetamido)cephalosporanic acid were used, and there was obtained 443 mg (yield: 64%) of a D(−)-7-[α-(4′-methoxychalocone-4-carboxamido)-phenylacetamido]cephalosporanic acid sodium salt as a white powder.

IR $\nu_{max}^{KBr}$ cm$^{-1}$: 1760, 1660(sh), 1640(sh), 1600
NMR(DMSO-d$_6$) δ:
1.98 (3H, s, COCH$_3$)
3.26 (2H, q, C$_2$—CH$_2$)
3.86 (3H, s, OCH$_3$)
4.88 (2H, q, C$_3'$—CH$_2$)
4.92 (1H, d, C$_6$—CH)
5.56 (1H, dd, C$_7$—CH)
5.92 (1H, d,

7.0-8.2 (15H, m's, aromatic and olefinic protons)
9.00 (1H, d, NH)
9.24 (1H, d, NH)

EXAMPLE 37

D(−)-7-[α-(2-chlorochalcone-4′-carboxamido)-phenylacetamido]cephalosporanic acid sodium salt:

The same procedure was repeated as in Example 5 with the exception that 286.5 mg of 2-chlorochalcone-4′-carboxylic acid and 306 mg of D(−)-7-(α-aminophenylacetamido)cephalosporanic acid were used, and there was obtained 592 mg (yield: 85%) of a D(−)-7-[α-(2-chlorochalcone-4′-carboxamido)phenylacetamido]-cephalosporanic acid sodium salt as a white powder.

IR $\nu_{max}^{KBr}$ cm$^{-1}$: 1760, 1660(sh), 1640(sh), 1600
NMR(DMSO-d$_6$) δ:
1.98 (3H, s, COCH$_3$)
3.26 (2H, q, C$_2$—CH$_2$)
4.88 (2H, q, C$'_3$—CH$_2$)
4.92 (1H, d, C$_6$—CH)
5.58 (1H, dd, C$_7$—CH)
5.92 (1H d,

7.3-7.6 (8H, m's, aromatic and olefinic protons)
8.0-8.2 (7H, m's, aromatic and olefinic protons)
9.2 (2H, d's, NH's)

EXAMPLE 38

D(−)-7-[α-(4-chlorochalcone-4′-carboxamido)-phenylacetamido]cephalosporanic acid:

The same procedure was repeated as in Example 33 with the exception that 286.5 mg of 4-chlorochalcone-4′-carboxylic acid and 406 mg of D(−)-7-(α-aminophenylacetamido)cephalosporanic acid were used, and there was obtained 229 mg (yield: 34%) of D(−)-7-[α-(4-chlorochalcone-4′-carboxamido)phenylacetamido]-cephalosporanic acid as a white powder.

IR $\nu_{max}^{KBR}$ cm$^{-1}$: 1780, 1730, 1660, 1630
NMR(DMSO-d$_6$) δ:
2.02 (3H, s, COCH$_3$)
3.46 (2H, broad s, C$_2$—CH$_2$)
4.80 (2H, q, C$_3'$—CH$_2$)
5.04 (1H, d, C$_6$—CH)
5.76 (1H, dd, C$_7$—CH)
5.90 (1H, d,

7.3-8.3 (15H, m's, aromatic and olefinic protons)
9.08 (1H, d, NH)
9.30 (1H, d, NH)

EXAMPLE 39

D(−)-7-[α-[p-(5-phenylpenta-2,4-dienoyl)benzamido]phenylacetamido]cephalosporanic acid sodium salt:

The same procedure was repeated as in Example 5 with the exception that 278 mg of p-(5-phenylpenta-2,4-dienoyl)benzoic acid and 406 mg of D(−)-7-(α-aminophenylacetamido)cephalosporanic acid were used, and there was obtained 579 mg of a D(−)-7-[α-[p-(5-phenylpenta-2,4-dienoyl)benzamido]phenylacetamido]cephalosporanic acid sodium salt as a yellow powder.

IR $\nu_{max}^{KBr}$ cm$^{-1}$: 1760, 1660(sh), 1640(sh), 1580
NMR(DMSO-d$_6$) δ:
1.98 (3H, s, COCH$_3$)
3.26 (2H, q, C$_2$—CH$_2$)
5.0 (3H, m's, C$_3$—CH$_2$ and C$_6$—CH)
5.62 (1H, dd, C$_7$—CH)
5.98 (1H, d,

7.3-7.7 (14H, m's, aromatic and olefinic protons)
8.16 (4H, s, aromatic protons)
9.3 (2H d's, NH's)

EXAMPLE 40

D(−)-7-[α-[p-[β-(2-furyl)acryloyl]benzamido]-phenylacetamido]-cephalosporanic acid sodium salt:

The same procedure was repeated as in Example 5 with the exception that 242 mg of p-[β-(2-furyl)acryloyl]benzoic acid and 406 mg of D(−)-7-(α-aminophenylacetamido)cephalosporanic acid were used, and there was obtained 535 mg (yield: 82%) of a D(−)-7-[α-[p-[β-(2-furyl)acryloyl]-benzamido]phenylacetamido]-cephalosporanic acid sodium salt as a white powder.

IR $\nu_{max}^{KBr}$ cm$^{-1}$: 1760, 1660(sh), 1640(sh), 1600
NMR(DMSO-d$_6$) δ:
1.98 (3H, s, COCH$_3$)
3.26 (2H, q, C$_2$—CH$_2$)
4.88 (2H, q, C$_3'$—CH$_2$)
4.92 (1H, d, C$_6$—CH)
5.56 (1H, dd, C$_7$—CH)

5.92 (1H, d,

6.68 (1H, dd, aromatic proton)
7.12 (1H, d, aromatic proton)
7.3–8.1 (12H, m's, aromatic and olefinic protons)
9.2 (2H d's, NH's)

EXAMPLE 41

D(−)-7-[α-[p-[β-(2-thienyl)acryloyl]benzamido]-phenylacetamido]cephallosporanic acid sodium salt:

The same procedure was repeated as in Example 5 with the exception that 258 mg of p-[β-(2-thienyl)acryloyl]benzoic acid and 406 mg of D(−)-7-(α-aminophenylacetamido)cephalosporanic acid were used, and there was obtained 534 mg (yield: 80%) of a D(−)-7-[α[p-[β-(2-thienyl)acryloyl]-benzamido]-phenylacetamido]cephalosporanic acid sodium salt as a pale yellow powder.

IR $\nu_{max}^{KBr}$ cm$^{-1}$: 1760, 1660(sh), 1640(sh), 1590
NMR(DMSO-d$_6$) δ:
1.98 (3H, s, COCH$_3$)
3.26 (2H, q, C$_2$—CH$_2$)
4.86 (2H, q, C$_3$+—CH$_2$)
4.92 (1H, d, C$_6$—CH)
5.56 (1H, dd, C$_7$—CH)
5.92 (1H, d,

7.2–8.2 (14H, m's, aromatic and olefinic protons)
9.2 (2H, d's , NH's)

EXAMPLE 42

D(−)-7-[α-[p-[3-(2-thienyl)propa-1-ene-3-onyl]benzamido]phenylacetamido]cephalosporanic acid:

The same procedure was repeated as in Example 33 with the exception that 258 mg of p-[3-(2-thienyl)propa-1-ene-3-onyl]benzoic acid and 406 mg of D(−)-7-(α-aminophenylacetamido)cephalosporanic acid were used, and there was obtained 255 mg (yield: 39%) of D(−)-7-[α-[p-3-(2-thienyl)-propa-1-ene-3-onyl]benzamido]phenylacetamido]cephalosporanic acid as a powder.

EXAMPLE 43

D(−)-7-[α-(6-styrylnicotinamido)phenylacetamido]-cephalosporanic acid: The same procedure was repeated as in Example 33 with the exception that 225 mg of 6-styrylnicotinic acid and 406 mg of D(−)-7-(α-aminophenylacetamido)cephalosporanic acid were used, and there was obtained 248 mg (yield: 40%) of D(−)-7-α-(6-styrylnicotinamido)phenylacetamido]-cephalosporanic acid as a pale yellow powder.

IR $\nu_{max}^{KBr}$ cm$^{-1}$: 1760, 1730, 1650(sh), 1630
NMR(DMSO-d$_6$) δ:
2.00 (3H, s, COCH$_3$)
3.46 (2H, broad s, C$_2$—CH$_2$)
4.84 (2H, q, C$_3$'—CH$_2$)
5.08 (1H, d, C$_6$—CH)
5.80 (1H, dd, C$_7$—CH)
5.92 (1H, d,

8.3–7.9 (13H, m's, aromatic and olefinic protons)
8.34 (1H, dd, aromatic proton)
9.12 (1H, d, aromatic proton
9.16 (1H, d, NH)
9.38 (1H, d, NH)

EXAMPLE 44

D(−)-7-[α-(2'-hydroxychalcone-4-carboxamido)-phenylacetamido]cephalosporanic acid sodium salt:

The same procedure was repeated as in Example 5 with the exception that 268 mg of 2'-hydroxychalcone-4-carboxylic acid and 406 mg of D(−)-7-(α-aminophenylacetamido)cephalosporanic acid were used, and there was obtained 473 mg (yield: 70%) of a D(−)-7-[α-(2'-hydroxychalcone-4-carboxamido)-phenylacetamido]cephalosporanic acid sodium salt as a pale yellow powder.

IR $\nu_{max}^{KBr}$ cm$^{-1}$: 1760, 1600(sh), 1640, 1600
NMR(DMSO-d$_6$) δ:
1.98 (3H, s, COCH$_3$)
3.26 (2H, q, C$_2$—CH$_2$)
4.9 (3H, m's, CH$_3$'—CH$_2$ and C$_6$—CH)
5.6 (1H, m, C$_7$—CH)
5.94 (1H, d,

6.9–8.2 (15H, m's, aromatic and olefinic protons)
9.10 (1H, d, NH)
9.30 (1H, d, NH)

EXAMPLE 45

D(−)-7-[α-[p-(2-thien-2-ylethenyl)benzamido]-phenylacetamido]cephalosporanic acid sodium salt:

The same procedure was repeated as in Example 5 with the exception that 230 mg of p-(2-thien-2-ylethenyl)-benzoic acid and 406 mg of D(−)-7-(α-aminophenylacetamido)cephalosporanic acid were used, and there was obtained 304 mg (yield: 48%) of a D(−)-7-[α-[p-(2-thien-2-ylethenyl)benzamido]phenylacetamido]-cephalosporanic acid sodium salt as a white powder.

IR $\nu_{max}^{KBr}$ cm$^{-1}$: 1760, 1660(sh), 1640(sh), 1600
NMR(DMSO-d$_6$) δ:
1.98 (3H, s, COCH$_3$)
3.26 (2H, q, C$_2$—CH$_2$)
4.86 (2H, q, C$_3$'—CH$_2$)
4.90 (1H , d, C$_6$—CH)
5.6 (1H, m, C$_7$—CH)
5.88 (1H, d,

6.9–8.0 (14H, m's, aromatic and olefinic protons)
8.9 (1H, d, NH)
9.3 (1H, d, NH)

EXAMPLE 46

D(−)-7-[60 -[6-(2-thien-2-ylethenyl)nicotinamido]-phenylacetamido]cephalosporanic acid:

The same procedure was repeated as in Example 33 with the exception that 231 mg of 6-(2-thien-2-ylethenyl)-nicotinic acid and 406 mg of D(−)-7-(α-aminocephalosporanic acid were used, and there was obtained 252 mg (yield: 41%) of D(−)-7-[α-[6-(2-thien-2-ylethenyl)nicotinamido]phenylacetamido]cephalosporanic acid as a yellow powder.

IR $\nu_{max}^{KBr}$ cm$^{-1}$: 1760, 1740, 1660(sh), 1630
NMR(DMSO-d$_6$) δ:
2.00 (3H, s, COCH$_3$)
3.46 (2H, broad s, C$_2$—CH$_2$)
4.80 (2H, q, C$_3'$—CH$_2$)
5.04 (1H, d, C$_6$—CH)
5.74 (1H, dd, C$_7$CH)
5.86 (1H, d,

7.0–7.6 (10H, m's, aromatic and olefinic protons)
7.94 (1H, d, olefinic proton)
8.24 (1H, dd, aromatic proton)
9.00 (1H, d, aromatic proton)
9.06 (1H, d, NH)
9.30 (1H d, NH)

EXAMPLE 47

D(−)-7-[α-[p-(4-phenylbuta-1,3-dienyl)benzamido]-phenylacetamido]cephalosporanic acid:

The same procedure was repeated as in Example 33 with the exception that 125 mg of p-(4-phenylbuta-1,3-dienyl)-benzoic acid and 203 mg of D(−)-7-(α-aminophenylacetamido)-cephalosporanic acid were used, and there was obtained 135 mg (yield: 42%) of D(−)-7-[α-[p-(4-phenylbuta-1,3-dienyl)benzamido]-phenylacetamido]cephalosporanic acid as a pale yellow powder.

IR $\nu_{max}^{KBr}$ cm$^{-1}$: 1780, 1720, 1660(sh), 1630
NMR(DMSO-d$_6$) δ:
2.02 (3H, s, COCH$_3$)
3.46 (2H, q, C$_2$—CH$_2$)
4.82 (2H, q, C$_3'$CH$_2$)
5.06 (1H, d, C$_6$—CH)
5.76 (1h, dd, C$_7$—CH)
5.88 (1H, d,

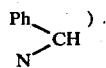

6.7–8.0 (18H, m's, aromatic and olefinic protons)
8.82 (1H, d, NH) 9.28 (1H, d, NH)

EXAMPLE 48

D(−)-7-[α-[6-(4-phenylbuta-1,3-dienyl)-nicotinamido]phenylacetamido]-cephalosporanic acid:

The same procedure was repeated as in Example 33 with the exception that 126 mg of 6-(4-phenylbuta-1,3-dienyl)nicotinic acid and 203 mg of D(−)-7-(α-aminophenylacetamido)cephalosporanic acid were used, and there was obtained 320 mg (yield: 100%) of D(−)-7-[α-[6-(4-phenylbuta-1,3-dienyl)nicotinamido]-phenylacetamido]cephalosporanic acid as a yellow powder.

IR $\nu_{max}^{KBr}$ cm$^{-1}$: 1770, 1730, 1660(sh), 1630
NMR(DMSO-d$_6$)δ:
2.00 (3H, s, COCH$_3$)
3.44 (2H, broad s, C$_2$-CH$_2$)
4.88 (2H, q, C$_3'$-CH$_2$)
5.04 (1H d, C$_6$-CH)
5.74 (1H, dd, C$_7$-CH)
5.86 (1h, d,

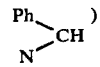

6.8–7.7 (15H, m's, aromatic and olefinic protons)
8.22 (1H, dd, aromatic proton)
9.00 (1H, d, aromatic proton)
9.06 (1H, d, NH)
9.30 (1H, d, NH)

EXAMPLE 49

D(−)-7-[α-(chalcone-4-carboxamido)-phenylacetamido]-3-deacetoxy-cephalosporanic acid potassium salt:

The same procedure was repeated as Example 5 with the exception that 252 mg of chalcone-4-carboxylic acid, 348 mg of D(−)-7-(α-aminophenylacetamido)-3-deacetoxy-cephalosporanic acid and 200 mg of a 2-ethyl-hexanoic acid potassium salt were used, and there was obtained 207 mg (yield: 33%) of a D(−)-7-[α-(chalcone-4-carboxamido)phenylacetamido]-3-deacetoxy-cephalosporanic acid potassium salt as a white powder.

IR $\nu_{max}^{KBr}$ cm$^{-1}$: 1760, 1660(sh), 1640(sh), 1600
NMR(DMSO-d$_6$) δ:
1.88 (3H, s, C$_3'$—CH$_3$)
3.14 (2H, q, C$_2$—CH$_2$)
4.84 (1H, d, C$_6$—CH)
5.48 (1H, dd, C$_7$—CH)
5.92 (1H, d,

7.2–8.2 (6H, m's, aromatic and olefinic protons)
9.0–9.4 (2H, m's, NH's)

EXAMPLE 50

D(−)-7-[α-(chalcone-4'-carboxamido)-phenylacetamido]-3-deacetoxy-cephalosporanic acid sodium salt:

The same procedure was repeated as in Example 5 with the exception that 252 mg of chalcone-4'-carboxylic acid and 366 mg of D(−)-7-(α-aminophenylacetamido)-3-deacetoxy-cephalosporanic acid monohydrate were used, and there was obtained 485 mg (yield: 80%) of a D(−)-7-[α-(chalcone-4'-carboxamido)phenylacetamido]-3-deacetoxy-cephalosporanic acid sodium salt as a pale yellow powder.

IR $\nu_{max}^{KBr}$ cm$^{-1}$: 1750, 1660, 1630, 1600
NMR(DMSO-d$_6$) δ:
1.92 (3H, s, C$_3'$—CH$_3$)
3.16 (2H, q, C$_2$—CH$_2$)
4.82 (1H, d, C$_6$—CH)
5.44 (1H, dd, C$_7$—CH)
5.90 (1H, d,

7.2–8.2 (16H, m's, aromatic and olefinic protons)

9.1 (2H, m's, NH's)

EXAMPLE 51

D(−)-7-[α-(4-styrylbenzamido)phenylacetamido]-3-deacetoxy-cephalosporanic acid:

The same procedure was repeated as in Example 33 with the exception that 224 mg of 4-styrylbenzoic acid and 366 mg of D(−)-7-(α-aminophenylacetamido)-3-deacetoxy-cephalosporanic acid monohydrate were used, and there was obtained 324 mg (yield: 58%) of D(−)-7-[α-(4-styrylbenzamido)phenylacetamido]-3-deacetoxy-cephalosporanic acid as a white powder.

IR $\nu_{max}^{KBr}$ cm$^{-1}$: 1770, 1660(sh), 1630
NMR(DMSO-d$_6$) δ:
1.98 (3H, s, C$_3'$—CH$_3$)
3.36 (2H, q, C$_2$—CH$_2$)
5.00 (1H, d, C$_6$—CH)
5.68 (1H, dd, C$_7$—CH)
5.92 (1H, d,

7.3–8.0 (16H, m's, aromatic and olefinic protons)
8.84 (1H, d, NH)
9.26 (1H, d, NH)

EXAMPLE 52

D(−)-7-[α-(4'-methoxychalcone-4-carboxamido)-phenylacetamido]-3-deacetoxy-cephalosporanic acid sodium salt:

The same procedure was repeated as in Example 5 with the exception that 292 mg of 4'-methoxychalcone-4-carboxylic acid and 366 mg of D(−)-7-(α-aminophenylacetamido)-3-deacetoxy-cephalosporanic acid monohydrate were used, and there was obtained 424 mg (yield: 67%) of a D(−)-7-[α-(4'-methoxychalcone-4-carboxamido)phenylacetamido]-3-deacetoxy-cephalosporanic acid sodium slt as a white powder.

IR $\nu_{max}^{KBr}$ cm$^{-1}$: 1770, 1660(sh), 1640(sh), 1610
NMR(DMSO-d$_6$) δ:
1.90 (3H, s, C$_3'$—CH$_3$)
3.16 (2H, q, C$_2$—CH$_2$)
3.86 (3H, s, OCH$_3$)
4.84 (1H, d, C$_6$—CH)
5.46 (1H, dd, C$_7$—CH)
5.92 (1H, d,

7.0–8.1 (15H, m's, aromatic and olefinic protons)
8.96 (1H, d, NH)
9.16 (1H, d, NH)

EXAMPLE 53

D(−)-7-[α-(2-chlorochalcone-4'-carboxamido)-phenylacetamido]-3-deacetoxy-cephalosporanic acid:

The same procedure was repeated as in Example 33 with the exception that 286.5 mg of 2-chlorochalcone-4'-carboxylic acid and 366 mg of D(−)-7-(α-aminophenylacetamido)cephalosporanic acid monohydrate were used, and there was obtained 453 mg (yield: 74%) of D(−)-7-[α-(2-chlorochalcone-4'-carboxamido)-phenylacetamido]-3-deacetoxy-cephalosporanic acid as a white powder.

IR $\nu_{max}^{KBr}$ cm$^{-1}$: 1770, 1660(sh), 1630
NMR(DMSO-d$_6$) δ:
1.98 (3H, s, C$_3'$—CH$_3$)
3.36 (2H, q, C$_2$—CH$_2$)
4.98 (1H, d, C$_6$—CH)
5.66 (1H, dd, C$_7$—CH)
5.92 (1H, d,

7.3–7.6 (8H, m's, aromatic and olefinic protons)
8.0–8.3 (7H, m's, aromatic and olefinic protons)
9.08 (1H, d, NH)
9.16 (1H, d, NH)

EXAMPLE 54

D(−)-7-[α-(4-chlorochalcone-4'-carboxamido)-phenylacetamido]-3-deacetoxy-cephalosporanic acid:

The same procedure was repeated as in Example 33 with the exception that 286.5 mg of 4-chlorochalcone-4'-carboxylic acid and 366 mg of D(−)-7-(α-aminophenylacetamido)cephalosporanic acid monohydrate were used, and there was obtained 235 mg (yield: 38%) of D(−)-7-[α-(4-chlorochalcone-4'-carboxamido)-phenylacetamido]-3-deacetoxy-cephalosporanic acid as a pale yellow powder.

IR $\nu_{max}^{KBr}$ cm$^{-1}$: 1770, 1660, 1630
NMR(DMSO-d$_6$) δ:
2.00 (3H, s, C$_3'$—CH$_3$)
3.36 (2H, q, C$_2$—CH$_2$)
4.98 (1H, d, C$_6$—CH)
5.66 (1H, dd, C$_7$—CH)
5.96 (1H, d,

7.2–8.2 (15H, m's, aromatic and olefinic protons)
9.08 (1H, d, NH)
9.16 (1H, d, NH)

What is claimed is:

1. Penicillin derivatives and non-toxic salts thereof represented by the formula (I).

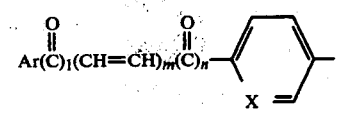

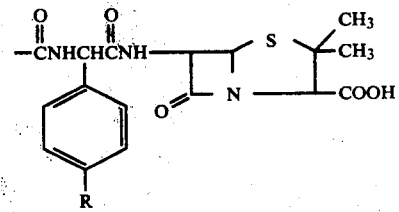

wherein Ar represents a phenyl or furyl, thienyl or pyridyl group which may be substituted by a halogen atom, hydroxy or lower alkoxy group, R represents a hydrogen atom or a hydroxy group, X represents CH or N, l and n are integers equal to 0 or 1 wherein the sum of l and n is 0 or 1, and m is an integer equal to 1 or 2.

2. Penicillin derivatives and non-toxic salt thereof represented by the formula (II),

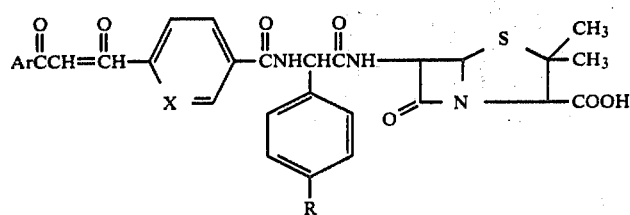

wherein Ar represents a phenyl or furyl, thienyl or pyridyl group which may be substituted by a halogen atom, hydroxy or lower alkoxy group, R represents a hydrogen atom or a hydroxy group, X represents CH or N.

3. The compound of claim 2 which is D(—)-α-(chalcone-4-carboxamido)-benzylpenicillin potassium salt.

4. The compound of claim 2 which is D(—)-α-(chalcone-4-carboxamido)-p-hydroxy benzylpenicillin potassium salt.

5. Penicillin derivatives and non-toxic salts thereof represented by the formula (III),

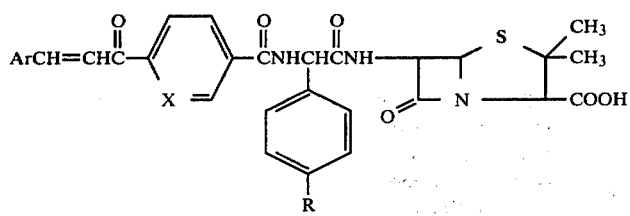

wherein Ar represents a phenyl or heterocyclic furyl, thienyl or pyridyl group which may be substituted by a halogen atom, hydroxy or lower alkoxy group, R represents a hydrogen atom or a hydroxy group, X represents CH or N.

6. The compound of claim 5 which is D(—)-α-(2-chlorochalcone-4′-carboxamido) benzylpenicillin sodium salt.

7. The compound of claim 5 which is D(—)-α-(4-chlorochalcone-4′-carboxamido) benzylpenicillin sodium salt.

8. The compound of claim 5 which is D(—)-α-(4-chlorochalcone-4′-carboxamido) p-hydroxybenzylpenicillin sodium salt.

9. The compound of claim 5 which is D(—)-α-[p-[β-(2-thienyl)acryloyl]benzamido]benzylpenicillin sodium salt.

10. The compound of claim 5 which is D(—)-α-[p-[β-(2-pyridyl)acryloyl]benzamido]benzylpenicillin sodium salt.

11. Penicillin derivatives and non-toxic salts thereof represented by the formula (IV).

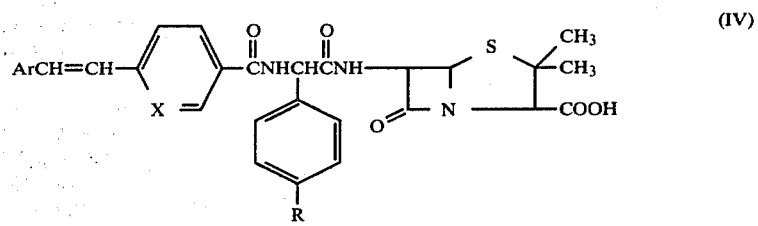

wherein Ar represents a phenyl or furyl, thienyl or pyridyl group which may be substituted by a halogen atom, hydroxy or lower alkoxy group, R represents a hydrogen atom or a hydroxy group, X represents CH or N.

12. The compound of claim 11 which is D(—)-α-(p-styrylbenzamido)-benzylpenicillin sodium salt.

13. The compound of claim 11 which is D(—)-α-(p-styrylbenzamido)p-hydroxy benzylpenicillin sodium salt.

14. Penicillin derivatives and non-toxic salts thereof represented by the formula (V),

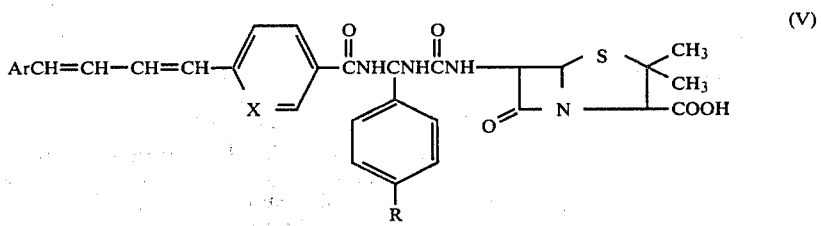

wherein Ar represents a phenyl or furyl, thienyl or pyridyl group which may be substituted by a halogen atom, hydroxy or lower alkoxy group, R represents a hydrogen atom or a hydroxy group, X represents CH or N.

15. The compound of claim 14 which is D(−)-α-[p-(5-phenylpenta-2,4-dienoyl)benzamido]benzylpenicillin sodium salt.

16. Penicillin derivatives and non-toxic salts thereof represented by the formula (VI),

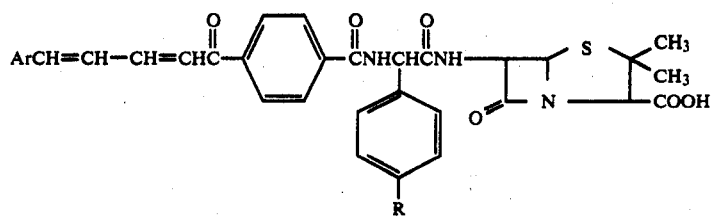

wherein Ar represents a phenyl or furyl, thienyl or pyridyl group which may be substituted by a halogen atom, hydroxy or lower alkoxy group, R represents a hydrogen atom or a hydroxy group, X represents CH or N.

* * * * *